(12) United States Patent
Ma

(10) Patent No.: US 9,084,793 B2
(45) Date of Patent: Jul. 21, 2015

(54) METHODS FOR TREATING ALZHEIMER'S DISEASE BY ADMINISTERING CERTAIN SYNTHETIC COMPOUNDS

(71) Applicant: BEIJING JOEKAI BIOTECHNOLOGY LLC, Beijing (CN)

(72) Inventor: Weiwei Ma, Kunshan (CN)

(73) Assignee: Bejing Joekai Biotechnology LLC, Beijing (CN)

( * ) Notice: Subject to any disclaimer, the term of this patent is extended or adjusted under 35 U.S.C. 154(b) by 0 days.

(21) Appl. No.: 14/374,573

(22) PCT Filed: Jan. 25, 2013

(86) PCT No.: PCT/IB2013/000458
§ 371 (c)(1),
(2) Date: Jul. 25, 2014

(87) PCT Pub. No.: WO2013/111013
PCT Pub. Date: Aug. 1, 2013

(65) Prior Publication Data
US 2015/0011550 A1    Jan. 8, 2015

Related U.S. Application Data

(63) Continuation-in-part of application No. PCT/US2012/022646, filed on Jan. 26, 2012.

(60) Provisional application No. 61/436,363, filed on Jan. 26, 2011.

(51) Int. Cl.
| | | |
|---|---|---|
| *A61K 31/34* | (2006.01) | |
| *A61K 31/404* | (2006.01) | |
| *A61K 31/496* | (2006.01) | |
| *A61K 31/535* | (2006.01) | |
| *A61K 31/5377* | (2006.01) | |
| *A61K 31/341* | (2006.01) | |
| *A61K 31/495* | (2006.01) | |
| *A61K 9/00* | (2006.01) | |

(52) U.S. Cl.
CPC ........... *A61K 31/5377* (2013.01); *A61K 9/0012* (2013.01); *A61K 31/34* (2013.01); *A61K 31/341* (2013.01); *A61K 31/404* (2013.01); *A61K 31/495* (2013.01); *A61K 31/496* (2013.01); *A61K 31/535* (2013.01)

(58) Field of Classification Search
CPC ... A61K 31/34; A61K 31/404; A61K 31/496; A61K 31/535
See application file for complete search history.

(56) References Cited

U.S. PATENT DOCUMENTS

| | | |
|---|---|---|
| 7,449,442 B2 | 11/2008 | He |
| 2003/0194403 A1 | 10/2003 | vandeWinkel |
| 2003/0232741 A1 | 12/2003 | Neufeld |
| 2013/0302337 A1 | 11/2013 | Zhong |

FOREIGN PATENT DOCUMENTS

| | | |
|---|---|---|
| CN | 1055930 | 11/1991 |
| CN | 101273962 | 10/2008 |
| EP | 0454385 | 10/1991 |
| WO | 03068147 | 8/2003 |
| WO | 2007008338 | 1/2007 |
| WO | 2008003317 | 1/2008 |
| WO | 2010048446 | 4/2010 |
| WO | 2012103282 | 8/2012 |

OTHER PUBLICATIONS

Birnbaum, A et al., Current Treatment Options in Oncology, vol. 6, No. 1, Jan. 2005, pp. 75-81, abstract only.
Bunney, T.D. et al., Nature Reviews Cancer, vol. 10, May 2010, pp. 342-352.
Ceresoli, G.L. et al., Annals of Oncology, vol. 15, 2004, pp. 1042-1047.
Chiang, H.C. et al., PNAS, vol. 107, No. 15, Apr. 13, 2010, pp. 7060-7065.
Chiang, H.C. et al., The FASEB Journal, vol. 23, Jun. 2009, pp. 1969-1977.
Cohen, E. et al., Cell, Dec. 11, 2009, vol. 139, No. 6, pp. 1157-1169.
Dahlgren, K.N. et al., The Journal of Biological Chemistry, vol. 277, No. 35, Aug. 30, 2002, pp. 32046-32053.
Entire patent prosecution history of U.S. Appl. No. 13/949,403, filed Jul. 24, 2013, entitled, "Methods and Compositions for Treating Alzheimer's Disease" at Non-Final Office Action mailed Oct. 7, 2014.
Entire patent prosecution history of U.S. Appl. No. 13/949,403, filed Jul. 24, 2013, entitled, "Methods and Compositions for Treating Alzheimer's Disease" at Response to Restriction filed Jul. 31, 2014.
Entire patent prosecution history of U.S. Appl. No. 13/949,403, filed Jul. 24. 2013, entitled, "Methods and Compositions for Treating Alzheimer's Disease" at Response to Restriction filed Jul. 31, 2014.
Entire patent prosecution history of U.S. Appl. No. 13/949,403, filed Jul. 24, 2013, entitled, "Methods and Compositions for Treating Alzheimer's Disease" at Restriction Requirement mailed Jun. 2, 2014.
European Search Report mailed Nov. 27, 2014 for European Application No. 12739544.0.
Fan, Q.W. et al., Current Top Microbial. Immunology, vol. 347, 2010, pp. 279-296.
Franke, T.F., Oncogene, vol. 27, 2008, pp. 6473-6488.
Gschwind, A. et al., Nature Reviews Cancer, vol. 4, No. 5, May 2004, pp. 361-370.
Heimberger, A.B. et al., Clinical Cancer Research, vol. 8, Nov. 2002, pp. 3496-3502.

(Continued)

*Primary Examiner* — Yong Chong
(74) *Attorney, Agent, or Firm* — RatnerPrestia

(57) ABSTRACT

Use of a synthetic compound selected from the group consisting of JKF-006, JKF-011 and JKF-027 in the preparation of a medicament for treating Alzheimer's disease.

2 Claims, 5 Drawing Sheets

(56) References Cited

OTHER PUBLICATIONS

Iijima, K. et al., PLoS ONE, vol. 3, No. 2, Feb. 2008, e1703.
Iijima, K. et al., PNAS, vol. 101, No. 17, Apr. 27, 2004, pp. 6623-6628.
International Preliminary Report on Patentability issued Jul. 29, 2014 for International Application No. PCT/IB2013/000458.
International Preliminary Report on Patentability issued Jul. 30, 2013 for International Application No. PCT/US2012/022646.
International Search Report mailed Aug. 15, 2013 for International Application No. PCT/IB2013/000458.
International Search Report mailed Aug. 22, 2012 for International Application No. PCT/US2012/022646.
Jankowsky, J.L. et al., Biomolecular Engineering, vol. 17, 2001, pp. 157-165.
Jankowsky, J.L. et al., The Journal of Neuroscience, vol. 25, No. 21, May 25, 2005, pp. 5217-5224.
Jensen, M.T. et al., Neuroscience, vol. 130, No. 3, 2005, pp. 667-684.
Lauren, J. et al., Nature, vol. 457, Feb. 26, 2009, pp. 1128-1132.
Martinez-Coria, H. et al., The American Journal of Pathology, vol. 176, No. 2, Feb. 2010, pp. 870-880.
Outeiro, T.F. et al., Science, vol. 317, Jul. 27, 2007, pp. 516-519.
Reiserer, R.S. et al., Genes Brain and Behavior, vol. 6, 2007, pp. 54-65.
RN 330861-11-5 Registry ED Entered STN: Apr. 11, 2001.
RN 335207-38-0 Registry ED Entered STN: May 11, 2001.
Rojas, M. et al., The Journal of Biological Chemistry, vol. 271, No. 44, Apr. 2005, pp. 27456-27461.
Savonenko, A. et al., Neurobiol Dis, vol. 18, No, 3., Apr. 2005, pp. 602-617.
Scholtzova, H. et al., Journal of Neuroscience Research, vol. 86, No. 12, Sep. 2008, pp. 2784-2791.
Sharma, S.V. et al., Nature Reviews Cancer, vol. 7, Mar. 2007, pp. 169-181.
Tully, T. et al., Journal of Comparative Physiology A, vol. 157, No. 2, 1985, pp. 263-277.
Wakeling, A.E. et al., Cancer Research, vol. 62, Oct. 15, 2002, pp. 5749-5754.
Wang, L. et al., PNAS, vol. 109, No. 41, Oct. 9, 2012, pp. 16743-16748.
"Epidermal Growth Factor Receptor" from Wikipedia, http://en.wikipedia.org/wiki/Epidermal_growth_factor_receptor, dated Jan. 3, 2011, pp. 1-38.

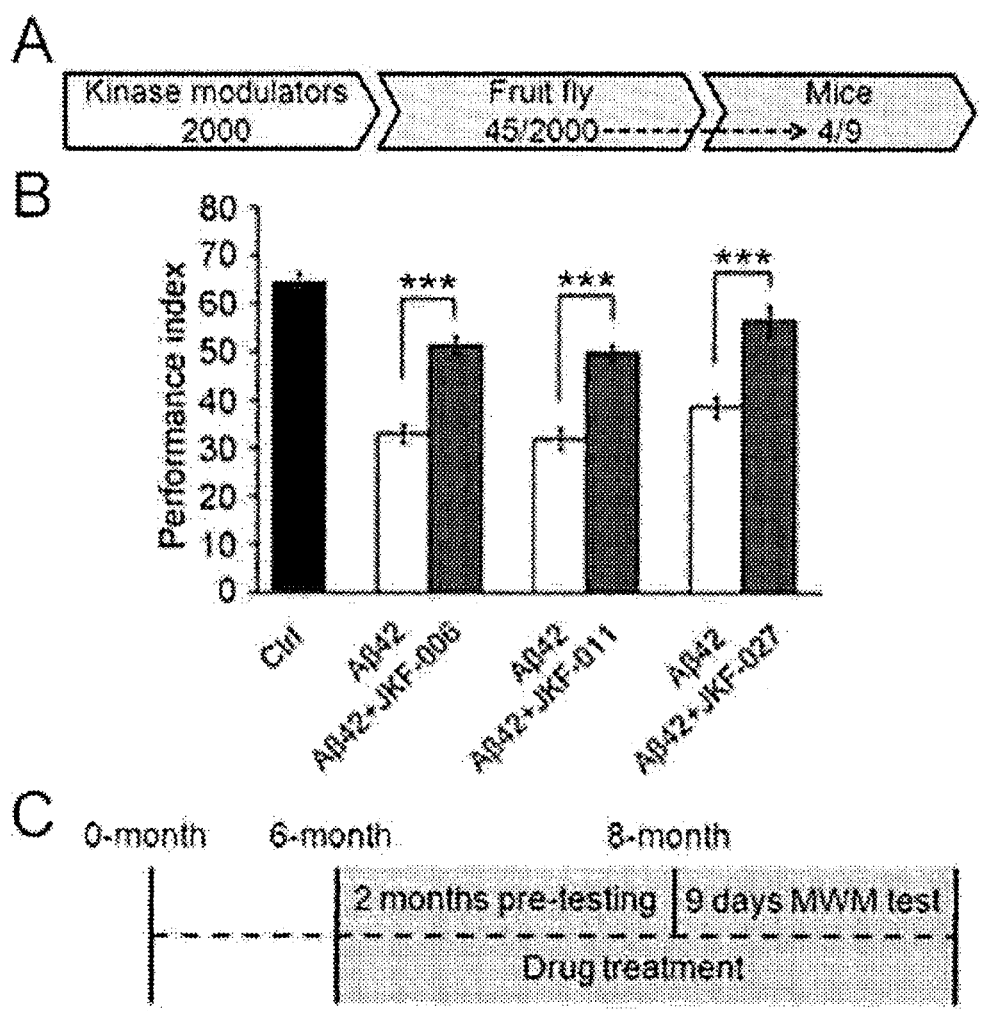
Fig.1A-C

Figure 1D-F
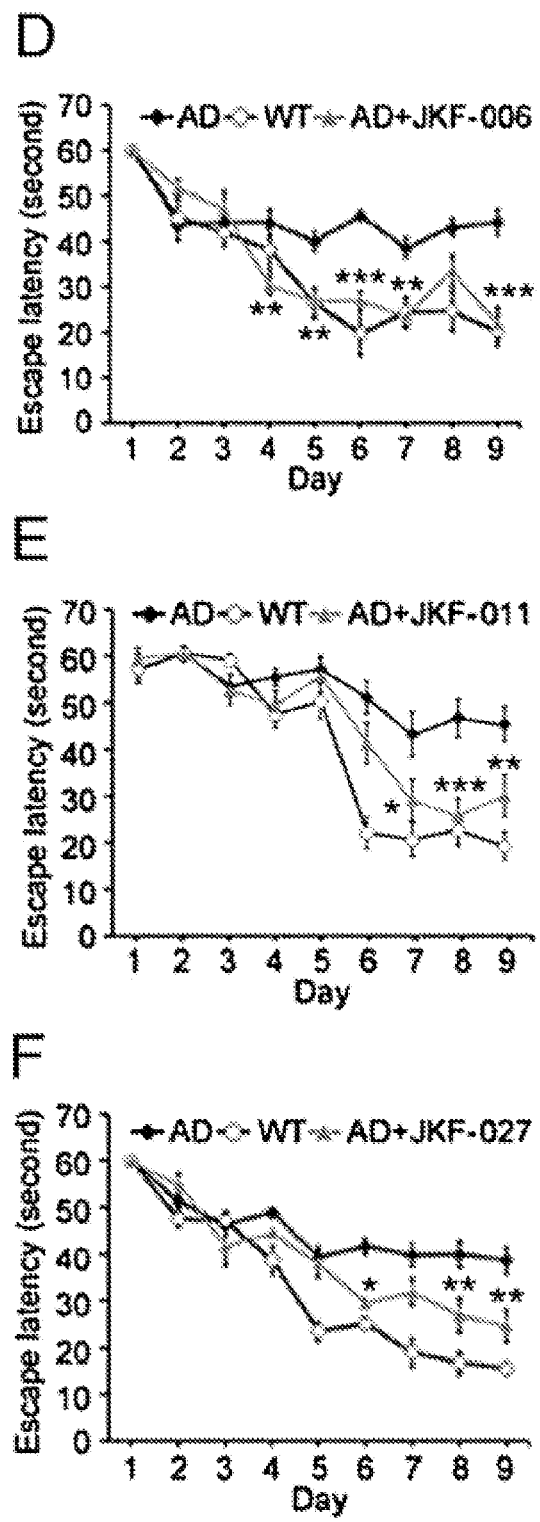

H

METHODS FOR TREATING ALZHEIMER'S DISEASE BY ADMINISTERING CERTAIN SYNTHETIC COMPOUNDS

The present application is a U.S. National Phase Application of PCT International Application PCT/IB2013/000458, filed Jan. 25, 2013, which is a continuation-in-part application of International Application PCT/US2012/022646 filed on Jan. 26, 2012, which claims priority US. Provisional Application No. 61/436,363 filed Jan. 26, 2011, the contents of each of which are incorporated herein in their entireties for all purposes.

CROSS REFERENCE TO RELATED APPLICATIONS

The present application claims the benefit of International Application PCT/US2012/022646 filed on Jan. 26, 2012.

FIELD OF THE DISCLOSURE

This disclosure relates to treatment of Alzheimer's disease. In particular, the disclosure relates to identification of certain synthetic compounds and use of these compounds for treating Alzheimer's disease.

BACKGROUND ART

Alzheimer's disease is the most common form of dementia, and is a progressive disease that causes memory loss, confusion, and a decline in functioning. To date there is no cure for the disease, and there is a tremendous need for effective treatment for the disease. A *Drosophila* model of Alzheimer's disease (AD) has been reported (Iijima et al., *PNAS* 101 (17): 6623-6628, 2004; Iijima et al., *PLoS ONE* 3(2): e1703, 2008), in which pan-neuronal expression of a secretary form of Aβ42 leads to phenotypes that recapitulate major features of AD clinical symptoms, including age-dependent memory loss, neurodegeneration, and accumulation of Aβ deposits.

SUMMARY OF THE DISCLOSURE

This disclosure is directed to identification of certain synthetic compounds and use of these compounds for treating Alzheimer's disease. In specific embodiments, this disclosure provides a method of treating Alzheimer's disease in a subject by administering an effective amount of a synthetic compound to the subject. Suitable synthetic small molecule compounds for use in the method of this disclosure include, e.g., JKF-006, JKF-011, and JKF-027.

BRIEF DESCRIPTION OF THE DRAWINGS

FIG. 1A-H. Behavioral screening of synthetic compounds. (A) Schematic illustration of screening processes and summary of results. (B) Prevention of Aβ42-induced memory loss in *Drosophila*. Effects of four representative compounds are shown. Concentrations: 50 μg/ml. N=6-8. (C) Drug feeding scheme for double transgenic mice. The age-matched mice (6-month old) were subject to two-month drug treatment and then to MWM test. (D-F) Rescue of Aβ-induced memory loss in mouse. The three compounds as in B are shown. Concentrations (in mg/kg/day) are 58 for JKF-006, 14 for JKF-011, 55 for JKF-027. N=6-9. (G) Effects of three positive compounds on oligomeric Aβ42-induced increase of p-EGFR activity in COS-7 cells transfected with an EGFR$^{wt}$ plasmid. The three compounds were capable of inhibiting induced p-EGFR activity. N=3. (H) Drug feeding protocol.

DETAILED DESCRIPTION

Figure 1G:
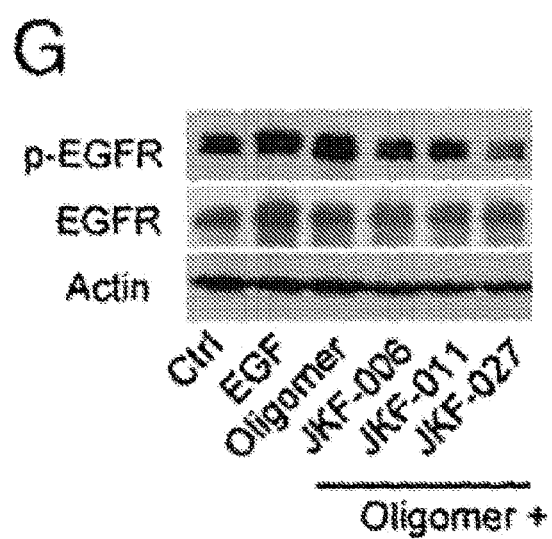

It has been further demonstrated herein that synthetic compounds JKF-006, JKF-011 and JKF-027 were effective in rescuing memory loss in a mouse and *Drosophila* model of AD. Accordingly, this disclosure provides methods and related compositions for treating Alzheimer's disease based on administration of these compounds.

As used herein, "treating Alzheimer's disease" means herein delaying the onset, slowing down the progression, and/or ameliorating the symptoms of the disease.

Alzheimer's disease is the most common form of dementia, and its symptoms are well recognized clinically. Early stage symptoms include inability to acquire new memories, for example, difficulty in recalling recent events and inability to acquire new information. As the disease progresses, the impairment of learning and memory becomes more pronounced, symptoms can include language impairment (including speech difficulties, and loss of reading and writing skills), loss of long term memory, loss of motor coordination, and behavioral and neuropsychiatric symptoms such as confusion, irritability, aggression, mood swings and general withdrawal. Advanced stage is characterized by the loss of verbal language ability, deterioration of muscle mass and mobility, and loss of other bodily functions.

By "delaying" the onset of Alzheimer's disease, it is meant that the therapeutic methods provided herein can postpone, hinder, or slow the development of the disease such that the probability of early disease symptoms manifesting in a subject, or the probability of the occurrences of the disease among multiple subjects, within a given time frame, is reduced when compared to not using the methods provided herein.

By "slowing down the progression" of Alzheimer's disease, it is meant that the pharmaceutical compositions and therapeutic methods provided herein effectively inhibit the progressive decline of the learning, memory, or language ability or other bodily functions.

By "ameliorating the symptoms" of the disease, it is meant that the pharmaceutical compositions and therapeutic methods provided herein reduce disease symptoms, and/or improve the learning, memory, or language ability or other bodily functions.

The term "subject" as used herein refers to any mammalian subject. In one embodiment, the subject is a human subject.

By "small molecule compounds" it is meant small organic compounds or salts thereof, generally having a molecular weight of less than 1500 daltons, preferably less than 1000 daltons, more preferably less than 800 daltons.

In some embodiments, synthetic compounds suitable for use in the present methods include JKF-006 (Benzoic acid, 4-chloro-3[5-[2-cyano-3-[(4-fluorophenyl)amino]-3-oxo-1-propen-1-yl]-2-furanyl]), JKF-011 (Piperazin-2-one), and JKF-027 (2-Propenamide, 2-cyano-N-[2-(1H-indol-3-yl)ethyl]-3-[5-(4-morpholinyl)-2-furanyl]), and pharmaceutically acceptable salts thereof, or a combination thereof. In specific embodiments, suitable compounds for use in the treatment are JKF-006, JKF-011, and JKF-027.

A suitable compound can be combined with a pharmaceutically acceptable carrier to provide a pharmaceutical composition. Pharmaceutically acceptable carriers include solvents, dispersion media, isotonic agents and the like. Except insofar as any conventional media, agent, diluent or carrier is detrimental to the recipient or to the therapeutic effectiveness of the active ingredients contained therein, its use is appropriate. The carrier can be liquid, semi-solid, e.g. pastes, or solid carriers. Examples of carriers include oils, water, oil/water emulsions, saline solutions, alcohol, sugar, gel, lipids, liposomes, resins, porous matrices, binders, fillers, coatings, preservatives and the like, or combinations thereof.

A suitable compound can be combined with a carrier in any convenient and practical manner, e.g., by admixture, solution, suspension, emulsification, encapsulation, absorption and the like, and can be made in formulations such as tablets, capsules, powder, syrup, suspensions that are suitable for injections, implantations, inhalations, ingestions or the like, using conventional formulation methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

This disclosure provides a method of treating Alzheimer's disease by administering a therapeutically effective amount of a suitable synthetic compound.

The term "therapeutically effective amount" means the amount required to achieve beneficial results in treating Alzheimer's disease as defined herein, i.e., to delay the onset, slow down the progression or ameliorate the symptoms of the disease, after given to the recipient for an appropriate period of time.

The precise amount of a suitable synthetic compound to be therapeutically effective may vary, depending on the nature of the active ingredient, the health and conditions of the recipient, and the route of administration, but can be determined by a skilled practitioner. For example, in some embodiments, the method provided herein for treating Alzheimer's disease involves administration to a patient of a synthetic compound at an amount ranging from 0.5 to 100 mg/day/person, and in some embodiments, from 1 to 50 mg/day/person, for example, 1, 5, 10, 15, 20 and 25 mg/day/person, or an amount between any of the two values listed above.

A suitable synthetic compound, optionally provided in a pharmaceutically acceptable carrier, can be given once or multiple times daily, every other day, or any other appropriate dosing schedule, and can be administered to the subject by any appropriate route, including the oral, parenteral (e.g., intravenous, intraperitoneal, intradermal, subcutaneous or intramuscular), intracranial, intracerebral, or intraspinal route.

The invention is further illustrated by the following, non-limiting examples.

EXAMPLE

*Drosophila* Stocks

Human wild type Aβ42 transgenic fly (UAS-Aβ42) used herein has been previously described (Iijima et al., *PLoS ONE* 3(2): e1703, 2008).

Pavlovian Olfactory Associative Immediate Memory

The training and testing procedures were the same as previously described (Tully and Quinn, *J Comp Physiol A* 157: 263-277, 1985). During one training session, a group of about 100 flies was sequentially exposed for 60 seconds to two odors, 3-octanol (OCT, Fluka) or 4-methylcyclohexanol (MCH, Fluka), with 45 seconds of fresh air in between. Flies were subjected to foot-shock (1.5 seconds pulses with 3.5 seconds intervals, 60 V) during exposure to the first odor (CS+) but not to the second (CS−). To measure "immediate memory" (also referred to as "learning"), flies were transferred immediately after training to the choice point of a T-maze and forced to choose between the two odors for 2 min. Then flies were trapped in their respective T-maze arms, anesthetized, and counted. A performance index (PI) was calculated from the distribution of this group of flies in the T-maze. A reciprocal group of flies was trained and tested by using OCT as the CS+ and MCH as the CS+, respectively. The so-called half-PIs, (OCT) and PI (MCH), were finally averaged for an n=1 and multiplied by 100. A PI of 0 indicated a distribution of 50:50 (no learning), while a PI of 100 indicated "perfect learning" that 100% of the flies avoided the CS+ previously paired with foot shock. Control groups are age-matched to the experimental groups in each test.

Mouse Strain

An AD-model mouse which expressed a mutant chimeric mouse/human APPswe and a mutant human presenilin 1 (Delta E9), both driven by the prion protein promoter, was purchased from the Jackson laboratory [strain B6C3-Tg (APPswe.PSEN1dE9) 85Dbo/J, or "double transgenic mouse"]. Transgenic mice were derived from B6C3/Tg+× B6C3 crosses. Genotyping was done by PCR following the Jackson Laboratory protocols.

The double transgenic mouse has been described in Jankowsky et al., *The Biomolecular Engineering* 17: 157-165, 2001. Extensive plaques are reported to be visible in early ages and the memory-loss phenotype is evident around 6-9 months old double transgenic mice (Jankowsky et al., supra; Reiserer, et al., *Genes Brain Behav* 6: 54-65, 2007; Savonenko et al., *Neurobiol Dis* 18: 602-617, 2005; Cohen et al., *Cell* 139: 1157-1169, 2009; Jankowsky et al., *J Neurosci* 25: 5217-5224, 2005).

Morris Water Maze

The Morris water maze experiment was performed following a procedure as previously reported (Jensen et al., *Neuroscience* 130: 667-684, 2005; Cohen et al., *Cell* 139: 1157-1169, 2009). Briefly, littermate 8-month-old mice (30-40 g in weight) were placed one animal per cage and fed in normal conditions. A water tank with 120 cm in diameter was filled with room temperature water (19-20° C.), which was made opaque withskim milk A transparent platform (Φ 15 cm) was located in the center of one of the four virtually divided quadrants and was submerged 2 cm below the water surface to be invisible. Distal cues were provided in all experiments as spatial references. Mice were let swim until they found the platform and allowed to stay for 5 seconds; if a mouse did not find the platform, it was gently guided to the platform and given the 5 s stay. Animals that did not find the platform were given a latency of 60 s. Mice were allowed to rest for 1 h between trials. Four trials were performed each day. In all experimental settings, a video tracking system was utilized (Jiliang Software Technology Co. Ltd., Shanghai, China). Latency to find the platform (maximum of 60 s) was recorded for each trial and the four daily trials were averaged for statistical analysis. Lavage of weight-matched drug diluted in physiological saline which containing 0.5% Tween-80 was carried out once each day from sixty days before training and testing till the end of experiments.

Statistical Analysis

All data were analyzed by student t test or one-way ANOVA following Bonferroni test (Origin version 8; OriginLab Corporation). Statistical results are presented as means±s.e.m. or as individual data (horizontal line) and mean (small square). Asterisks indicates critical values (*P<0.05, P<0.01 and *P<0.001).

Cell Culture, Transfection and Oligomer Treatment

COS-7 cells were cultured in normal Dulbecco's Modified Eagle Medium (D-MEM) containing 10% fetal bovine serum (Invitrogen) at 37° C. in 5% $CO_2$. Transfection of the cells with an $EGFR^{WT}$ plasmid was performed following the Lipofectamine 2000 manuals (Invitrogen). After 48 h, cells were washed with fresh medium once and incubated with 10 or 25 μg/ml Aβ42 oligomers for 15 min at 37° C. in 5% $CO_2$. 0.5 μg/ml human EGF (Sigma) was used as a positive control. Cells were then washed with PBS for 3 times and collected.

Preparation of Aβ42 Oligomers

The preparation procedure was described previously (Dahlgren K, et al., *J Biol Chem.* 277:32046-53, 2002). Synthetic and recombinant wild type Aβ42 (AnaSpec, Inc.) was initially dissolved to 1 mM in hexafluoroisopropanol (Sigma).

Hexafluoroisopropanol was removed under vacuum in a Speed Vac, and the peptide film was stored at −20° C. For oligomer preparation, the peptide was first resuspended in DMSO to a concentration of 12.5 mg/ml and then diluted with DMEM/F-12 (phenol red-free, Invitrogen) to a final concentration of 500 μg/ml and incubated at 4° C. for 24 h.

Western Blot Analysis

Whole fly head or cells lysates were prepared using a RIPA buffer containing 0.3% SDS, 50 mM Tris-HCl, pH 7.4, 0.5% NP-40, 1% sodium deoxycholate, 150 mM NaCl, 5 mM EDTA, 1 tablet per 50 ml complete protease inhibitor cocktail (Roche Diagnostics). Lysates were diluted in an SDS sample buffer and separated on 10-20% Tris-Tricine gels (Invitrogen), and transferred to nitrocellulose membranes (Invitrogen). The membranes were boiled in PBS for 3 min, blocked with 5% non-fat dry milk and blotted with a first antibody. First antibodies used included mouse anti-Aβ42 (6E10, Covance Research Products), mouse anti-dEGFR (Abcam), rabbit anti-hEGFR (Cell Signaling), mouse anti-hEGFR-p (Cell Signaling) and rabbit anti-Actin (Sigma). Data were analyzed with the ImageJ software (National Institutes of Health).

Behaviorally Identified Effective Synthetic Compounds Inhibit EGFR Activation

Figure 1H:
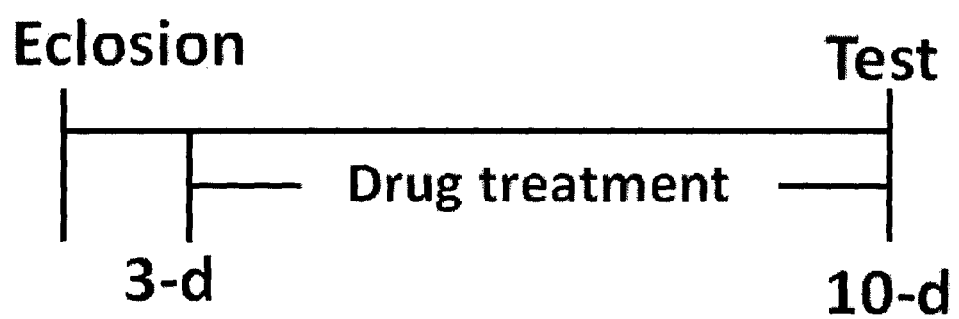
Figure 2:
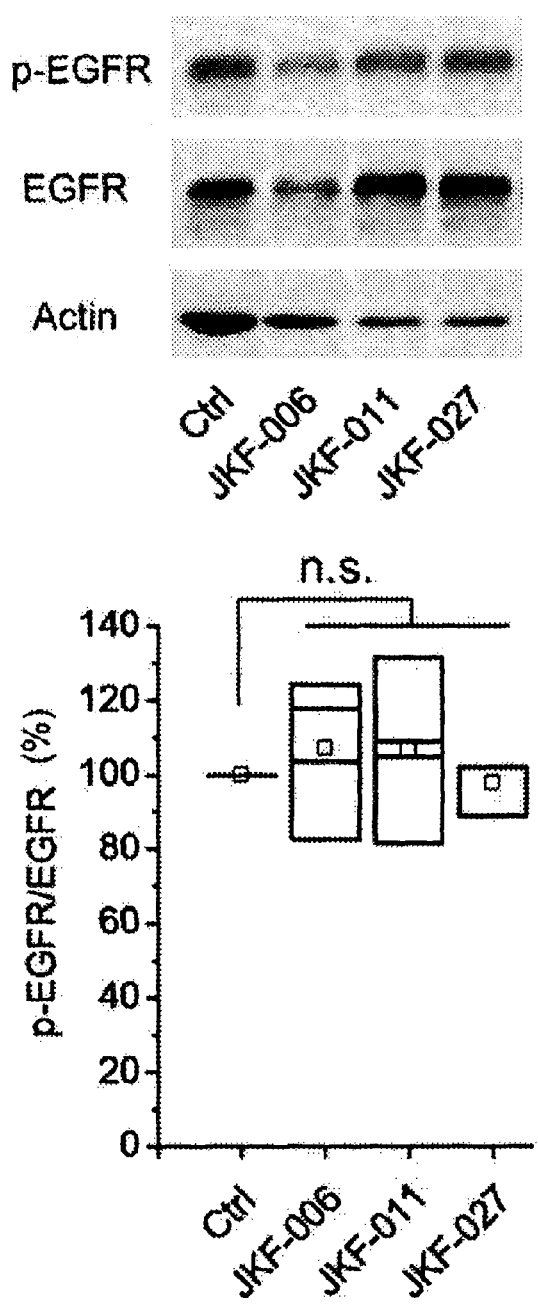
FIG. 2. Synthetic compounds do not influence the normal p-EGFR level. 100 μg/ml JKF-006, JKF-011 and JKF-027 were used to treat EGFR$^{wt}$-expressing COS-7 cells without oligomeric Aβ42 peptides. None of the compounds changed the p-EGFR level. N=3-4.

Behavioral screening was performed with 2000 synthetic compounds (purchased from TimTec LLC, USA) with structures that are presumably targeted to protein kinase activities (FIG. 1A). Only male flies were selected for 7-day drug treatment and then subjected to behavioral assay at day 10 after eclosion. The drug feeding protocol is indicated in FIG. 1H. Going through an initial n=2 screening followed with n>6 confirmation, 45 synthetic compounds were found to be effective in rescuing the memory loss in Aβ42 transgenic flies. Among them, 9 were tested in double transgenic mice and compounds were indicated to have positive results after 2 months of treatment (6- to 8-month-old) (FIG. 1A-G). Three compounds designated as JKF-006, JKF-011 and JKF-027 showed effective results in rescuing the memory loss. Subsequently, these three compounds were also shown to significantly inhibit a 10 μg/ml oligomeric Aβ42-induced phosphorylation of human EGFR expressed in COS-7 cells (FIG. 1G), but incapable of affecting the endogenous p-EGFR level (FIG. 2).

TABLE 1

Behaviorally screened synthetic compounds.

| JKF ID/CAS | Molecular Formula | MW | TimTec ID | Structure | Chemical Name |
|---|---|---|---|---|---|
| JKF-006 330861-11-5 | $C_{21}H_{12}ClFN_2O_4$ | 410.79 | ST026864 | 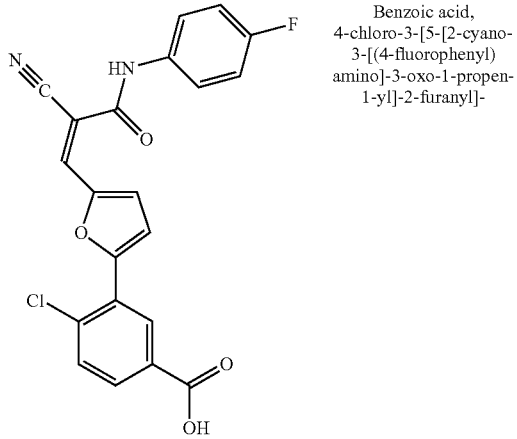 | Benzoic acid, 4-chloro-3-[5-[2-cyano-3-[(4-fluorophenyl)amino]-3-oxo-1-propen-1-yl]-2-furanyl]- |
| JKF-011 5625-67-2 | $C_4H_8N_2O$ | 100.12 | ST025752 | 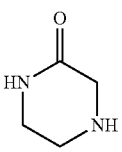 | Piperazin-2-one |

TABLE 1-continued

Behaviorally screened synthetic compounds.

| JKF ID/CAS | Molecular Formula | MW | TimTec ID | Structure | Chemical Name |
|---|---|---|---|---|---|
| JKF-027 335207-38-0 | C$_{22}$H$_{22}$N$_4$O$_3$ | 390.44 | ST052637 | 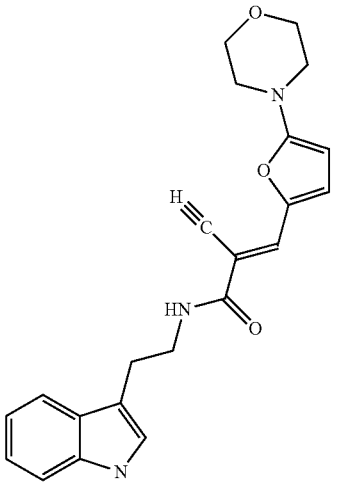 | 2-Propenamide, 2-cyano-N-[2-(1H-indol-3-yl)ethyl]-3-[5-(4-morpholinyl)-2-furanyl]- |

What is claimed is:

1. A method of treating Alzheimer's disease in a subject in need thereof, comprising administering to the subject an effective amount of a synthetic compound selected from the group consisting of JKF-006, JKF-011 and JKF-027.

2. The method of claim 1, wherein the compound is administered to the subject via oral or parental administration.

* * * * *